(12) United States Patent
Jiang et al.

(10) Patent No.: US 11,926,608 B2
(45) Date of Patent: Mar. 12, 2024

(54) SYNTHESIS METHOD AND DEVICE FOR RAPIDLY PRODUCING LACTIDE AT HIGH YIELD

(71) Applicants: NANJING UNIVERSITY, Nanjing (CN); NANJING QUANKAI RESEARCH INSTITUTE OF BIOMATERIALS CO., LTD., Nanjing (CN)

(72) Inventors: Wei Jiang, Nanjing (CN); Yunbiao Qi, Nanjing (CN); Ping Sun, Nanjing (CN); Wei Huang, Nanjing (CN); Aimin Li, Nanjing (CN); Quanxing Zhang, Nanjing (CN)

(73) Assignees: NANJING UNIVERSITY, Nanjing (CN); NANJING QUANKAI RESEARCH INSTITUTE OF BIOMATERIALS CO., LTD., Nanjing (CN)

( * ) Notice: Subject to any disclaimer, the term of this patent is extended or adjusted under 35 U.S.C. 154(b) by 468 days.

(21) Appl. No.: 17/249,524

(22) Filed: Mar. 4, 2021

(65) Prior Publication Data
US 2021/0188799 A1 Jun. 24, 2021

(51) Int. Cl.
*C07D 319/12* (2006.01)
*B01D 1/22* (2006.01)
(Continued)

(52) U.S. Cl.
CPC ............. *C07D 319/12* (2013.01); *B01D 1/22* (2013.01); *B01D 3/143* (2013.01); *B01D 5/006* (2013.01);
(Continued)

(58) Field of Classification Search
CPC ... B01D 1/00; B01D 1/22; B01D 3/00; B01D 3/14; B01D 3/143; B01D 5/00; B01D 5/0057; B01D 5/006; B01D 5/0075; B01D 5/0078; B01D 5/009; B01J 4/00; B01J 4/001; B01J 4/02; B01J 19/00; B01J 19/0006; B01J 19/0013; B01J 19/0053; B01J 19/0066; B01J 19/24; B01J 19/245; B01J 19/2455; B01J 19/2465; B01J 19/247; B01J 2219/00; B01J 2219/00002;
(Continued)

(56) References Cited

U.S. PATENT DOCUMENTS

5,136,057 A * 8/1992 Bhatia .................. C07D 319/12
562/580
7,488,783 B2 * 2/2009 Coszach ................ C08G 63/08
528/480
(Continued)

*Primary Examiner* — Natasha E Young
(74) *Attorney, Agent, or Firm* — CBM PATENT CONSULTING, LLC (57) ABSTRACT

The invention discloses a synthesis method and device for rapidly producing lactide at high yield. The method comprises: adding a single component of lactic acid or two components of lactic acid and catalyst, passing the mixture through a mixer to enter an oligomer preparation system, increasing a residence time through bottom circulation, synthesizing oligomeric lactic acid, and passing a gas-phase component through a rectification system. With the adoption of the device, the lactide is capable of being efficiently synthesized, crude lactide with a yield of 94% to 98% is capable of being obtained.

12 Claims, 1 Drawing Sheet

(51) Int. Cl.
    *B01D 3/14*     (2006.01)
    *B01D 5/00*     (2006.01)
    *B01J 4/00*     (2006.01)
    *B01J 19/00*     (2006.01)
    *B01J 19/24*     (2006.01)
    *C08G 63/91*     (2006.01)

(52) U.S. Cl.
CPC ........... *B01D 5/0075* (2013.01); *B01D 5/009* (2013.01); *B01J 4/001* (2013.01); *B01J 19/0013* (2013.01); *B01J 19/245* (2013.01); *C08G 63/912* (2013.01); *B01J 2219/0004* (2013.01); *B01J 2219/00081* (2013.01); *B01J 2219/00085* (2013.01)

(58) Field of Classification Search
CPC ...... B01J 2219/00027; B01J 2219/0004; B01J 2219/00049; B01J 2219/00051; B01J 2219/00074; B01J 2219/00076; B01J 2219/00081; B01J 2219/00085; B01J 2219/00162; B01J 2219/00186; C07D 319/00; C07D 319/10; C07D 319/12; C08G 63/00; C08G 63/02; C08G 63/06; C08G 63/08; C08G 63/88; C08G 63/91; C08G 63/912
See application file for complete search history.

(56) References Cited

U.S. PATENT DOCUMENTS

| | | | | |
|---|---|---|---|---|
| 8,859,245 | B2 * | 10/2014 | Uyama | B01D 11/0492<br>435/135 |
| 10,023,553 | B2 * | 7/2018 | De Vries | B01J 19/0013 |
| 2005/0222379 | A1 * | 10/2005 | Matsuo | B01J 19/1862<br>528/359 |

* cited by examiner

SYNTHESIS METHOD AND DEVICE FOR RAPIDLY PRODUCING LACTIDE AT HIGH YIELD

TECHNICAL FIELD

The present invention belongs to the field of synthesizing monomers from environmentally friendly/biomedical degradable materials, particularly relates to an efficient synthesis process of lactide, and specifically relates to a synthesis method and device for rapidly producing lactide at high yield.

BACKGROUND

With the development of times, non-degradable plastic based on petroleum is more and more widely used, which also brings many environmental pollution problems. Meanwhile, the demand for non-renewable petroleum resources of general plastic also affects a sustainable development problem. Polylactic acid is a green polymer material with wide application, which is suitable for extrusion, injection molding, and plastic molding, and after being discarded, the polylactic acid may be degraded into carbon dioxide and water in a natural environment, causing little environmental pollution, thus being one of the best choices to solve the "white pollution". The polylactic acid has a good mechanical strength, a chemical stability, a biocompatibility, and a bioabsorbability. Meanwhile, the polylactic acid is non-toxic and pollution-free, and a degradation product thereof may be used for human metabolism, so that the polylactic acid may be widely used in medical industry, agriculture, food packaging, daily necessities, and other fields.

At present, methods for synthesizing the polylactic acid mainly comprise a one-step method and a two-step method. According to the one-step method, lactic acid, glycolic acid, and derivatives thereof are used as raw materials to directly synthesize the polylactic acid, such as directly polycondensating the lactic acid into the polylactic acid in JP733861, JP599612, and CN198764C, which takes a long time, and has a low molecular weight and a low application value. According to the two-step method, the above raw materials are polycondensated and depolymerized to obtain lactide, and a refined and purified monomer is subjected to ring-opening polymerization to obtain the polylactic acid, such as U.S. Pat. No. 5,142,023, EP261572, JP564688B, and WO2009121830. The synthesized polylactic acid has a high relative molecular weight. At present, the two-step method is mainly used for synthesis in industry, and the preparation and purification of the lactide as a synthetic intermediate has become the focus of research. At present, the lactide has a long synthesis time, such as depolymerization for 40 minutes in ZL201510648014.9 and depolymerization for 1 hour to 4 hours in ZL201310146469.1, which may lead to a low efficiency and a high running cost after amplification.

SUMMARY

Objective of the invention: a synthesis method for rapidly producing lactide at high yield is provided to solve problems of a long residence time, a low efficiency, and a high cost in commercial lactide synthesis in the prior art, which shortens a residence time of a reactor, improves a yield, and provides a low-cost solution for industrial production of the lactide.

In order to achieve the above objective, the technical solutions adopted in the present invention are as follows.

A synthesis method for rapidly producing lactide at high yield comprises the following steps of:
a. using L-lactic acid, D-lactic acid, or DL-lactic acid as a raw material, carrying out a polymerization synthesis reaction at 100° C. to 180° C. under an absolute pressure of of 1 KPa to 100 KPa, improving a yield by recovering lactic acid from a light component, and improving a molecular weight of oligolactic acid through reflux a heavy component, so as to obtain oligolactic acid with a weight-average molecular weight of 500 Da to 3,000 Da;
b. purifying the oligolactic acid obtained in step (1) to remove unreacted lactic acid and water; and
c. depolymerizing the oligolactic acid purified in step (2) under an action of a catalyst at 200° C. to 260° C. under an absolute pressure of 0.1 KPa to 1 KPa, purifying and collecting the light component to obtain a lactide product, and refluxing and depolymerizing the heavy component again.

Further, in step (1), the polymerization synthesis reaction may also be carried out in the presence of an oligomerization catalyst, and the oligomerization catalyst comprises but is not limited to zinc oxide, zinc lactate, zinc acetate, zinc isooctanoate, zinc stearate, stannous oxide, stannous oxide, stannous octoate, stannous chloride, and other zinc or tin catalysts.

The present invention further provides a synthesis device for rapidly producing lactide at high yield, which comprises:
an oligomer preparation system used for carrying out a polymerization synthesis reaction with L-lactic acid, D-lactic acid, or DL-lactic acid as a raw material, so as to obtain oligolactic acid, and introducing a reaction product into an oligomer purification system;
the oligomer purification system used for purifying the reaction product introduced from the oligomer preparation system, removing unreacted lactic acid and water, and introducing the purified oligolactic acid into an oligomer depolymerization system;
the oligomer depolymerization system used for depolymerizing the purified oligolactic acid under an action of a catalyst, so as to obtain crude lactide, and introducing the crude lactide into a lactide purification system;
the lactide purification system used for purifying the crude lactide, so as to obtain a lactide product and a by-product, and introducing the by-product into a recovery system; and
the recovery system used for processing and utilizing the by-product.

Specifically, the oligomer preparation system comprises an oligomerization reactor, a raw material pump, an oligomerization catalyst feeding pump, a raw material mixer, an oligomerization discharging/circulating pump, a rectifying tower, and a condenser;
wherein, a lactic acid raw material (85% to 90% lactic acid solution) and an oligomerization catalyst respectively enter the raw material mixer through the raw material pump and the oligomerization catalyst feeding pump for mixing at the same time, and then the mixture is fed from a side face of the oligomerization reactor;
the oligomerization discharging/circulating pump is located on a discharging pipe at a bottom of the oligomerization reactor, and is connected with a feeding pipe of the oligomer purification system and a side line feeding port of the oligomerization reactor through a three-way valve, and a reflux ratio of an oligomer is controlled to be 20:1 to 1,000:1, preferably 30:1 to 700:1, and most preferably 50:1 to 200:1.

A feeding pipe of the rectifying tower is connected with a top of the oligomerization reactor, a discharging pipe at a top of the rectifying tower is connected with a condensate storage tank after passing through the condenser, and a side face of the condensate storage tank is connected with an oligomerization vacuum system; and a discharging pipe of the condensate storage tank is provided with a condensate circulating/discharging pump, which is connected to a side line feeding pipe of the rectifying tower through a three-way valve. An absolute pressure of the rectifying tower is controlled to be 1 KPa to 100 KPa, preferably 2 KPa to 50 KPa, and most preferably 5 KPa to 20 kPa by the oligomerization vacuum system; and a temperature of the rectifying tower is controlled to be 40° C. to 80° C. preferably 45° C. to 75° C. and most preferably 50° C. and 70° C.

Specifically, the oligomer purification system comprises an oligomer purification reactor, an oligomer discharging pump, and a purification condenser;

a side line feeding port of the oligomer purification reactor is connected with a discharging pipe of the oligomer preparation system; a discharging pipe at a top of the oligomer purification reactor is connected with a purification system condensate storage tank after passing through the purification condenser, and a side face of the purification system condensate storage tank is connected with an oligomer purification vacuum system; a discharging pipe at a bottom of the purification system condensate storage tank is provided with a purification system condensate discharging pump;

the oligomer discharging pump is located on a discharging pipe at a bottom of the oligomer purification reactor, and is connected with a feeding pipe of the oligomer depolymerization system; and The oligomer purification reactor is a packed rectifying tower; an absolute pressure of a tower top is controlled to be 1 KPa to 50 KPa, preferably 2 KPa to 30 KPa, and most preferably 3 KPa to 20 KPa by the oligomerization purification vacuum system; and a temperature of the tower top is controlled to be 20° C. to 70° C. preferably 20° C. to 50° C. and most preferably 20° C. to 40° C. so as to reduce impurities such as acid, water, and a part of small molecule polymer.

Specifically, the oligomer depolymerization system comprises a depolymerization reactor, a depolymerization catalyst feeding pump, a depolymerization feed mixer, and a depolymerized heavy component discharging/circulating pump.

Wherein, the oligomerization catalyst comprises but is not limited to zinc oxide, zinc lactate, zinc acetate, zinc isooctanoate, zinc stearate, stannous oxide, stannous oxide, stannous octoate, stannous chloride, and other zinc or tin catalysts. The depolymerization catalyst may be the oligomerization catalyst added before, and may be supplemented later. The depolymerization catalyst and a purified product produced by the oligomer purification system enter the depolymerization feed mixer through the depolymerization catalyst feeding pump for mixing at the same time, and then the mixture is fed from a side face of the depolymerization reactor. A reaction temperature of the depolymerization feed mixer is controlled to be 200° C. to 260° C. a residence time is 0.5 minute to 5 minutes, and an absolute pressure is 0.1 Kpa to 1 Kpa.

The depolymerized heavy component discharging/circulating pump is located on a discharging pipe at a bottom of the depolymerization reactor, and is connected to the depolymerization feed mixer through a three-way valve, a heavy component produced in the depolymerization reactor is returned to the depolymerization feed mixer to be mixed with a reaction raw material, and then the mixture enters the depolymerization reactor again for reaction; and a light component produced in the depolymerization reactor is connected with a feeding pipe of the lactide purification system through a discharging port above a side face of the depolymerization reactor to remove impurities such as lactic acid and water.

Specifically, the lactide purification system comprises a lactide purification reactor and a lactide storage tank;

The lactide storage tank is connected with a discharging port at a bottom of the lactide purification reactor, and a lactide product is conveyed outwards through the lactide discharging pump. Impurities such as lactic acid and water are removed through the lactide purification reactor, so as to obtain a lactide product with a content of L-lactide, D-lactide, or DL-lactide content of 94% to 98%, and a content of meso-lactide is 0.5% to 5.5%.

Uncondensed steam in the lactide purification reactor is connected to a feeding pipe of the recovery system through a by-product discharging port at a top of the lactide purification reactor.

Specifically, the recovery system comprises a recovery system reactor, a recovery liquid storage tank, and a recovery liquid discharging pump; and A side face of the recovery liquid storage tank is connected with a depolymerization vacuum system, and a feeding port at a top of the recovery liquid storage tank is connected with a discharging port at a bottom of the recovery system reactor. Uncondensed steam in the lactide purification reactor is recovered through the recovery system reactor, so as to obtain L-lactic acid, D-lactic acid, or DL-lactic acid solution with a concentration of 65% to 80%. The recovery liquid storage tank discharges a recovery liquid outwards through the recovery liquid discharging pump on a discharging pipe at a bottom of the recovery liquid storage tank.

Specifically, the oligomerization reactor or the depolymerization reactor is any one of a falling-film reactor, a thin film evaporation reactor, a packing reactor, and a double falling-film reactor.

The lactide purification reactor or the recovery system reactor is any one of a shell-and-tube heat exchanger, a plate heat exchanger, a spiral plate heat exchanger, and a tubular heat exchanger.

Beneficial Effects:

In the present invention, the lactic acid is used as the raw material for reaction, the oligomeric lactic acid is synthesized by polymerization first, then the oligomeric lactic acid is purified to remove unreacted lactic acid and water, and depolymerized under the action of the catalyst, so as to obtain the crude lactide, and finally, the crude lactide is purified to obtain the lactide product. The method is capable of effectively shortening a preparation time of the lactide and significantly improving a yield of the lactide.

In the present invention, a single component of lactic acid or the lactic acid is added into double components of a catalyst, the mixture passes through a mixer to enter the oligomer preparation system, a residence time is increased through bottom circulation, the oligomeric lactic acid is synthesized, and a gas-phase component passes through the rectification system to improve a yield of the oligomeric lactic acid; the oligomeric lactic acid passes through the purification device to remove unreacted lactic acid and water; and a catalyst is added into the refined oligomeric lactic acid, the mixture passes through a mixer, the mixture enters the depolymerization reactor to be depolymerized into lactide under certain absolute pressure and temperature conditions, the heavy component enters the depolymerization reactor again through reflux, so as to increase a yield of the lactide, and the light component passes through the purification and recovery system to obtain a lactide product. With the adoption of the device, the lactide is capable of being efficiently synthesized, crude lactide with a yield of 94% to 98% is capable of being obtained within a short residence time of 0.5 minute to 5 minutes, a molecular weight of the heavy-component polylactic acid is slowly increased, and the heavy-component polylactic acid is capable of being returned for depolymerization; after the light component passes through the simple purification system, a content of L-lactide, D-lactide or DL-lactide in the lactide product is 94% to 98%, and a content of meso-lactide is 0.5% to 5.5%, with a simple and rapid operation, a high yield, and easy industrialization.

BRIEF DESCRIPTION OF THE DRAWINGS

The present invention is further described in detail with reference to the accompanying drawings and the specific embodiments, and the advantages of the above and/or other aspects of the present invention will become clearer.

Figure 1:
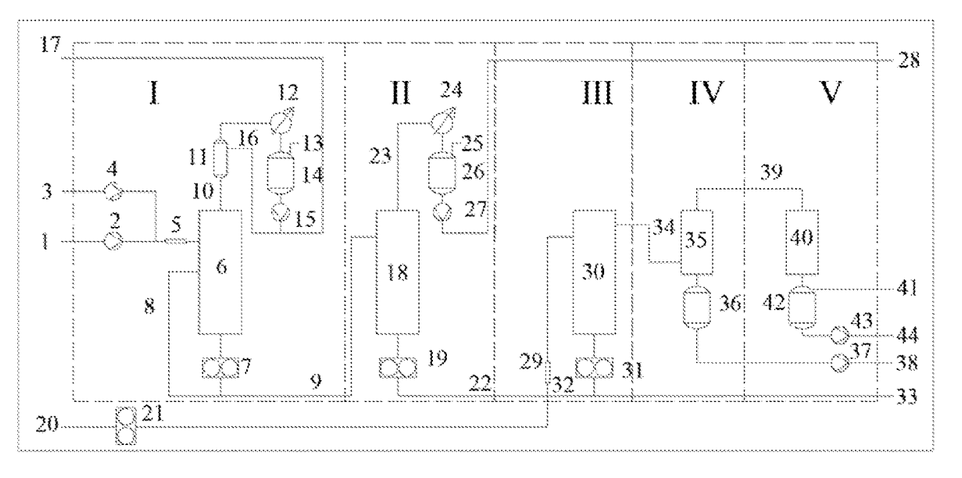
FIGURE is a schematic structure diagram of a synthesis device for rapidly producing lactide at high yield according to the present invention.

Wherein, the reference numerals are respectively represented as follows:

I refers to oligomer preparation system; II refers to oligomer purification system; III refers to oligomer depolymerization system; IV refers to lactide purification system; V refers to recovery system; 1 refers to lactic acid raw material; 2 refers to raw material pump; 3 refers to oligomerization catalyst; 4 refers to oligomerization catalyst feeding pump; 5 refers to raw material mixer; 6 refers to oligomerization reactor; 7 refers to oligomerization discharging/circulating pump; 8 refers to oligomeric circulating material; 9 refers to oligomer; 10 refers to gas-phase component; 11 refers to rectifying tower; 12 refers to condenser; 13 refers to oligomerization vacuum system; 14 refers to condensate storage tank; 15 refers to condensate circulating/discharging pump; 16 refers to circulating condensate; 17 refers to oligomerization condensate; 18 refers to oligomer purification reactor; 19 refers to oligomer discharging pump; 20 refers to depolymerization catalyst; 21 refers to depolymerization catalyst feeding pump; 22 refers to purified oligomer; 23 refers to oligomer light component; 24 refers to purification condenser; 25 refers to oligomerization purification vacuum system; 26 refers to purification system condensate storage tank; 27 refers to purification system condensate discharging pump; 28 refers to purification system condensate; 29 refers to depolymerization feed mixer; 30 refers to depolymerization reactor; 31 refers to depolymerized heavy component discharging/circulating pump; 32 refers to circulated and depolymerized heavy component; 33 refers to depolymerized heavy component; 34 refers to depolymerized light component; 35 refers to lactide purification reactor; 36 refers to lactide storage tank; 37 refers to lactide discharging pump; 38 refers to lactide product; 39 refers to uncondensed steam; 40 refers to recovery system reactor; 41 refers to depolymerization vacuum system; 42 refers to recovery liquid storage tank; 43 refers to recovery liquid discharging pump; and 44 refers to recovery liquid.

DETAILED DESCRIPTION

The present invention can be better understood according to the following embodiments.

The structure, scale, size, etc. shown in the accompanying drawings of the specification are only used to match with the contents disclosed in the specification for those skilled in the art to understand and read, and are not used to limit the executable limiting conditions of the present invention, thus having no technical substantive significance. Any structural modification, change of scale relationship, or adjustment of size shall still fall within the scope covered by the technical contents disclosed in the present invention without affecting the effect and the goal achieved by the present invention. Meanwhile, the terms such as "upper", "lower", "front", "rear", and "middle" cited in the specification are only for convenience of description and clarity, and are not used to limit the implementable scope of the present invention. The change or adjustment of the relative relationship shall be regarded as the implementable scope of the present invention without substantial change of technical content.

In the following embodiments, lactide is prepared by using a device shown in FIGURE. The device mainly comprises an oligomer preparation system I, an oligomer purification system II, an oligomer depolymerization system III, a lactide purification system IV, and a recovery system V. The oligomer preparation system I is used for carrying out a polymerization synthesis reaction with L-lactic acid, D-lactic acid, or DL-lactic acid as a raw material, so as to obtain oligolactic acid, and a reaction product is introduced into the oligomer purification system II. The oligomer purification system II is used for purifying the reaction product introduced from the oligomer preparation system I to remove unreacted lactic acid and water, and the purified oligolactic acid is introduced into the oligomer depolymerization system III. The oligomer depolymerization system III is used for depolymerizing the purified oligolactic acid under an action of a catalyst, so as to obtain crude lactide, and the obtained crude lactide is introduced into the lactide purification system IV. The lactide purification system IV is used for purifying the crude lactide, so as to obtain a lactide product and a by-product, and the by-product is introduced into the recovery system V. The recovery system V is used for processing and utilizing the by-product.

The oligomer preparation system I comprises an oligomerization reactor 6, a raw material pump 2, an oligomerization catalyst feeding pump 4, a raw material mixer 5, an oligomerization discharging/circulating pump 7, a rectifying tower 11, and a condenser 12. A lactic acid raw material 1 and an oligomerization catalyst 3 respectively enter the raw material mixer 5 through the raw material pump 2 and the oligomerization catalyst feeding pump 4 for mixing at the same time, and then the mixture is fed from a side face of the oligomerization reactor 6. The oligomerization discharging/circulating pump 7 is located on a discharging pipe at a bottom of the oligomerization reactor 6, and is connected with a feeding pipe of the oligomer purification reactor 18 and a side line feeding port of the oligomerization reactor 6 through a three-way valve, and a reflux ratio of an oligomer is controlled to be 20:1 to 1,000:1. A feeding pipe of the rectifying tower 11 is connected with a top of the oligomerization reactor 6, a discharging pipe at a top of the rectifying tower 11 is connected with a condensate storage tank 14 after passing through a condenser 12, and a side face of the condensate storage tank 14 is connected with an oligomerization vacuum system 13. A discharging pipe of the condensate storage tank 14 is provided with a condensate circulating/discharging pump 15, and is connected to a side line feeding pipe of the rectifying tower 11 through a three-way valve. An absolute pressure of the rectifying tower 11 is controlled to be 1 KPa to 100 KPa by the oligomerization vacuum system 13, and a temperature of the rectifying tower is controlled to be 40° C. to 80° C.

The oligomer purification system II comprises an oligomer purification reactor 18, an oligomer discharging pump 19, and a purification condenser 24. A side line feeding port of the oligomer purification reactor 18 is connected with a discharging pipe of the oligomerization reactor 6. A discharging pipe at a top of the oligomer purification reactor 18 is connected with the purification system condensate storage tank 26 after passing through the purification condenser 24, and a side face of the purification system condensate storage tank 26 is connected with the oligomer purification vacuum system 25. A discharging pipe at a bottom of the purification system condensate storage tank 26 is provided with a purification system condensate discharging pump 27. The oligomer discharging pump 19 is located on a discharging pipe at a bottom of the oligomer purification reactor 18, and is connected with a feeding pipe of the depolymerization reactor 30. The oligomer purification reactor 18 is a packed rectifying tower. An absolute pressure of a tower top is controlled to be 1 KPa to 50 KPa by the oligomerization purification vacuum system 25, and a temperature of the tower top is controlled to be 20° C. to 70° C. so as to reduce impurities such as acid, water, and a part of small molecular polymer.

The oligomer depolymerization system II comprises a depolymerization reactor 30, a depolymerization catalyst feeding pump 21, a depolymerization feed mixer 29, and a depolymerized heavy component discharge/circulation pump 31. The depolymerization catalyst 20 and a purified product produced by the oligomer purification reactor 18 enter the depolymerization feed mixer 29 through the depolymerization catalyst feeding pump 21 for mixing at the same time, and then the mixture is fed from a side face of the depolymerization reactor 30. A reaction temperature of the depolymerization feed mixer 29 is controlled to be 200° C. to 260° C., a residence time is 0.5 minute to 5 minutes, and an absolute pressure is 0.1 Kpa to 1 Kpa. The depolymerized heavy component discharging/circulating pump 31 is located on a discharging pipe at a bottom of the depolymerization reactor 30, and is connected to the depolymerization feed mixer 29 through a three-way valve, a heavy component produced in the depolymerization reactor 30 is returned to the depolymerization feed mixer 29 to be mixed with a reaction raw material, and then the mixture enters the depolymerization reactor 30 again for reaction. A light component produced in the depolymerization reactor 30 is connected with a feeding pipe of the lactide purification reactor 35 through a discharging port above a side face of the depolymerization reactor 30 to remove impurities such as lactic acid and water.

The lactide purification system IV comprises a lactide purification reactor 35 and a lactide storage tank 36. The lactide storage tank 36 is connected with a discharging port at a bottom of the lactide purification reactor 35, and the lactide product 38 is conveyed outwards through the lactide discharging pump 37. Impurities such as lactic acid and water are removed through the lactide purification reactor 35, so as to obtain a lactide product with a content of L-lactide, D-lactide, or DL-lactide content of 94% to 98%, and a content of meso-lactide is 0.5% to 5.5%. Uncondensed steam in the lactide purification reactor 35 is connected to a feeding pipe of the recovery system reactor 40 through a by-product discharging port at a top of the lactide purification reactor.

The recovery system V comprises a recovery system reactor 40, a recovery liquid storage tank 42, and a recovery liquid discharging pump 43. A side face of the recovery liquid storage tank 42 is connected with a depolymerization vacuum system 41, and a feeding port at a top of the recovery liquid storage tank is connected with a discharging port at a bottom of the recovery system reactor 40. Uncondensed steam in the lactide purification reactor 35 is recovered through the recovery system reactor 40, so as to obtain L-lactic acid, D-lactic acid, or DL-lactic acid solution with a concentration of 65% to 80%. The recovery liquid storage tank 42 discharges a recovery liquid 44 outwards through the recovery liquid discharging pump 43 on a discharging pipe at a bottom of the recovery liquid storage tank.

Embodiment 1

90% L-lactic acid raw material 1 entered an oligomerization reactor 6 at a flow rate of 10 g/h through a raw material pump 2. The oligomerization reactor 6 was a TLNS falling-film reactor, and the reactor was operated at 80° C. under an absolute pressure of 1 KPa for dehydration and oligomerization. A reflux ratio of a dehydrated oligomer was controlled to be 1,000:1 by an oligomerization discharging/circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 40° C. through reflux. A molecular weight of an oligomer 9 was 500 Da.

The oligomer 9 entered an oligomer purification reactor 18, the reactor was a RFJL packed rectifying tower with side line feeding, and was operated under an absolute pressure of 1 KPa, and a temperature of a tower top was 20° C. Removed acid, water, and dimer were purified and reused.

A purified oligomer 22 and a depolymerization catalyst zinc acetate 20 were mixed evenly by a depolymerization feed mixer 29, and then the mixture entered a depolymerization reactor 30 for depolymerization reaction under 0.1 KPa at 220° C. The depolymerization reactor 30 was a WEF thin film evaporation reactor, a residence time was controlled to be 2 minutes, and a reflux ratio of a depolymerized heavy component 33 was controlled to be 2:1 by a depolymerized heavy component discharging/circulating pump 31. After a refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common shell-and-tube heat exchanger of 0.1 m$^2$, and a heat exchange temperature was controlled to be 20° C. After purification, 6.775 g/h lactide product was obtained, with a yield of 94.1%, and a content of L-lactide was 98.1%.

Uncondensed steam 39 in a lactide purification reactor 35 entered a recovery system reactor 40, the reactor was a plate heat exchanger of 0.1 m$^2$, and a temperature of the heat exchanger was controlled to be 10° C. A recovery liquid was 0.1 g/h lactic acid solution, a concentration of the L-lactic acid was 70%, and the L-lactic acid was reused after purification.

Embodiment 2

90% L-lactic acid raw material 1 was mixed with a catalyst zinc oxide 3 at a flow rate of 20 g/h through a raw material pump 2, and then the mixture entered an oligomerization reactor 6. The oligomerization reactor 6 was a TLNS falling-film reactor, and the reactor was operated at 120° C. under an absolute pressure of 1 KPa for dehydration and oligomerization. A reflux ratio of a dehydrated oligomer was controlled to be 300:1 by an oligomerization discharging/circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 60° C. through reflux. A molecular weight of an oligomer 9 was 1,100 Da.

The oligomer 9 entered an oligomer purification reactor 18, the reactor was a RFJL packed rectifying tower with side line feeding, and was operated under an absolute pressure of 20 KPa, and a temperature of a tower top was 25° C. Removed acid, water, and dimer were purified and reused.

A purified oligomer 22 entered a depolymerization reactor 30 for depolymerization reaction under 0.2 KPa at 240° C. The depolymerization reactor 30 was a RFJL packing reactor, a residence time was controlled to be 1.5 minutes, and a reflux ratio of a depolymerized heavy component 33 was controlled to be 2:1 by a depolymerized heavy component discharging/circulating pump 31. After a refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common plate heat exchanger of 0.1 m², and a heat exchange temperature was controlled to be 60° C. After purification, 14.778 g/h lactide product was obtained, with a weight yield of 94.9%, and a content of L-lactide was 96.9%.

Uncondensed steam 39 in a lactide purification reactor 35 entered a recovery system reactor 40, the reactor was a spiral plate heat exchanger of 0.1 m², and a temperature of the heat exchanger was controlled to be 5° C. A recovery liquid was 0.2 g/h lactic acid solution, a concentration of the L-lactic acid was 65%, and the L-lactic acid was reused after purification.

Embodiment 3

90% L-lactic acid raw material 1 was mixed with a catalyst zinc acetate 3 at a flow rate of 50 g/h through a raw material pump 2, and then the mixture entered an oligomerization reactor 6. The oligomerization reactor 6 was a WEF thin film evaporation reactor, and the reactor was operated at 180° C. under an absolute pressure of 100 KPa for dehydration and oligomerization. A reflux ratio of a dehydrated oligomer was controlled to be 20:1 by an oligomerization discharging/circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 70° C. through reflux. A molecular of an oligomer 9 was 800 Da.

The oligomer 9 entered an oligomer purification reactor 18, the reactor was a RFJL packed rectifying tower with side line feeding, and was operated under an absolute pressure of 40 KPa, and a temperature of a tower top was 40° C. Removed acid, water, and dimer were purified and reused.

A purified oligomer 22 entered a depolymerization reactor 30 for depolymerization reaction under 1 KPa at 260° C. The depolymerization reactor 30 was a TLNS falling-film reactor, a residence time was controlled to be 1 minute, and a reflux ratio of a depolymerized heavy component 33 was controlled to be 0.5:1 by a depolymerized heavy component discharging/circulating pump 31. After a refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common spiral plate heat exchanger of 0.2 m², and a heat exchange temperature was controlled to be 20° C. After purification, 36.639 g/h lactide product was obtained, with a weight yield of 94.1%, and a content of L-lactide was 95.1%.

Uncondensed steam 39 in a lactide purification reactor 35 entered a recovery system reactor 40, the reactor was a tubular heat exchanger of 0.2 m², and a temperature of the heat exchanger was controlled to be 25° C. A recovery liquid was 0.4 g/h lactic acid solution, a concentration of the L-lactic acid was 80%, and the L-lactic acid was reused after purification.

Embodiment 4

90% L-lactic acid raw material 1 entered an oligomerization reactor 6 at a flow rate of 50 g/h through a raw material pump 2. The oligomerization reactor 6 was a WEF thin film evaporation reactor, and the reactor was operated at 170° C. under an absolute pressure of 50 KPa for dehydration and oligomerization. A reflux ratio of a dehydrated oligomer was controlled to be 50:1 by an oligomerization discharging/circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 80° C. through reflux. A molecular of an oligomer 9 was 1,200 Da.

The oligomer 9 entered an oligomer purification reactor 18, the reactor was a RFJL packed rectifying tower with side line feeding, and was operated under an absolute pressure of 50 KPa, and a temperature of a tower top was 70° C. Removed acid, water, and dimer were purified and reused.

A purified oligomer 22 and a depolymerization catalyst stannous octoate 20 were mixed evenly by a depolymerization feed mixer 29, and then the mixture entered a depolymerization reactor 30 for depolymerization reaction under 0.1 KPa at 230° C. The depolymerization reactor 30 was a WEF thin film evaporation reactor, a residence time was controlled to be 0.5 minute, and a reflux ratio of a depolymerized heavy component 33 was controlled to be 1:1 by a depolymerized heavy component discharging/circulating pump 31. After a refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common tubular heat exchanger of 0.2 m$^2$, and a heat exchange temperature was controlled to be 50° C. After purification, 36.879 g/h lactide product was obtained, with a weight yield of 94.1%, and a content of L-lactide was 97.8%.

Uncondensed steam 39 in a lactide purification reactor 35 entered a recovery system reactor 40, the reactor was a shell-and-tube heat exchanger of 0.2 m$^2$, and a temperature of the heat exchanger was controlled to be 20° C. A recovery liquid was 0.45 g/h lactic acid solution, a concentration of the L-lactic acid was 75%, and the L-lactic acid was reused after purification.

Embodiment 5

90% L-lactic acid raw material 1 entered an oligomerization reactor 6 at a flow rate of 50 g/h through a raw material pump 2. The oligomerization reactor 6 was a WEF thin film evaporation reactor, and the reactor was operated at 160° C. under an absolute pressure of 20 KPa for dehydration and oligomerization. A reflux ratio of a dehydrated oligomer was controlled to be 100:1 by an oligomerization discharging/ circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 60° C. through reflux. A molecular of an oligomer 9 was 1,500 Da.

The oligomer 9 entered an oligomer purification reactor 18, the reactor was a RFJL packed rectifying tower with side line feeding, and was operated under an absolute pressure of 20 KPa, and a temperature of a tower top was 40° C. Removed acid, water, and dimer were purified and reused.

A purified oligomer 22 and a depolymerization catalyst stannous octoate 20 were mixed evenly by a depolymerization feed mixer 29, and then the mixture entered a depolymerization reactor 30 for depolymerization reaction under 0.1 KPa at 250° C. The depolymerization reactor 30 was a RFJL packing reactor, a residence time was controlled to be 0.7 minute, and a reflux ratio of a depolymerized heavy component 33 was controlled to be 0.1:1 by a depolymerized heavy component discharging/circulating pump 31. After a refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common shell-and-tube heat exchanger of 0.2 m$^2$, and a heat exchange temperature was controlled to be 60° C. After purification, 37.121 g/h lactide product was obtained, with a weight yield of 95.4%, and a content of L-lactide was 96.2%.

Uncondensed steam 39 in a lactide purification reactor 35 entered a recovery system reactor 40, the reactor was a plate heat exchanger of 0.2 m$^2$, and a temperature of the heat exchanger was controlled to be 40° C. A recovery liquid was 0.3 g/h lactic acid solution, a concentration of the L-lactic acid was 85%, and the L-lactic acid was reused after purification.

Embodiment 6

90% L-lactic acid raw material 1 was mixed with a catalyst stannous octoate 3 at a flow rate of 50 g/h through a raw material pump 2, and then the mixture entered an oligomerization reactor 6. The oligomerization reactor 6 was a WEF thin film evaporation reactor, and the reactor was operated at 160° C. under an absolute pressure of 20 KPa for dehydration and oligomerization. A reflux ratio of a dehydrated oligomer was controlled to be 100:1 by an oligomerization discharging/circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 60° C. through reflux. A molecular of an oligomer 9 was 1,500 Da.

The oligomer 9 entered an oligomer purification reactor 18, the reactor was a RFJL packed rectifying tower with side line feeding, and was operated under an absolute pressure of 20 KPa, and a temperature of a tower top was 40° C. Removed acid, water, and dimer were purified and reused.

A purified oligomer 22 entered a depolymerization reactor 30 for depolymerization reaction under 0.2 KPa at 260° C. The depolymerization reactor 30 was a TLNS double-falling-film reactor, a residence time was controlled to be 0.5 minute, and a reflux ratio of a depolymerized heavy component 33 was controlled to be 0:1 by a depolymerized heavy component discharging/circulating pump 31. After the refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common plate heat exchanger of 0.2 m$^2$, and a heat exchange temperature was controlled to be 50° C. After purification, 37.297 g/h lactide product was obtained, with a weight yield of 95.9%, and a content of L-lactide was 95.2%.

Uncondensed steam 39 in a lactide purification reactor 35 entered a recovery system reactor 40, the reactor was a spiral plate heat exchanger of 0.2 m$^2$, and a temperature of the heat exchanger was controlled to be −20° C. A recovery liquid was 0.32 g/h lactic acid solution, a concentration of the L-lactic acid was 50 and the L-lactic acid was reused after purification.

Embodiment 7

90% L-lactic acid raw material 1 entered an oligomerization reactor 6 at a flow rate of 30 g/h through a raw material pump 2. The oligomerization reactor 6 was a RFJL packing reactor, and the reactor was operated at 170° C. under an absolute pressure of 50 KPa for dehydration and oligomerization. A reflux ratio of a dehydrated oligomer was controlled to be 80:1 by an oligomerization discharging/circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 60° C. through reflux. A molecular of an oligomer 9 was 1,600 Da.

The oligomer 9 entered an oligomer purification reactor 18, the reactor was a RFJL packed rectifying tower with side line feeding, and was operated under an absolute pressure of 15 KPa, and a temperature of a tower top was 35° C. Removed acid, water, and dimer were purified and reused.

A purified oligomer 22 and a depolymerization catalyst zinc lactate 20 were mixed evenly by a depolymerization feed mixer 29, and then the mixture entered a depolymerization reactor 30 for depolymerization reaction under 0.1 KPa at 260° C. The depolymerization reactor 30 was a TLNS falling-film reactor, a residence time was controlled to be 1.0 minute, and a reflux ratio of a depolymerized heavy component 33 was controlled to be 0:1 by a depolymerized heavy component discharging/circulating pump 31. After the refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common spiral plate heat exchanger of 0.2 m$^2$, and a heat exchange temperature was controlled to be 60° C. After purification, 22.877 g/h lactide product was obtained, with a weight yield of 98.0%, and a content of L-lactide was 96.4%.

Uncondensed steam 39 in a lactide purification reactor 35 entered a recovery system reactor 40, the reactor was a tubular heat exchanger of 0.2 m$^2$, and a temperature of the heat exchanger was controlled to be 10° C. A recovery liquid was 0.11 g/h lactic acid solution, a concentration of the L-lactic acid was 75%, and the L-lactic acid was reused after purification.

Embodiment 8

90% L-lactic acid raw material 1 entered an oligomerization reactor 6 at a flow rate of 30 g/h through a raw material pump 2. The oligomerization reactor 6 was a RFJL packing reactor, and the reactor was operated at 160° C. under an absolute pressure of 50 KPa for dehydration and oligomerization. A reflux ratio of a dehydrated oligomer was controlled to be 200:1 by an oligomerization discharging/circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 60° C. through reflux. A molecular of an oligomer 9 was 3,000 Da.

The oligomer 9 entered an oligomer purification reactor 18, the reactor was a RFJL packed rectifying tower with side line feeding, and was operated under an absolute pressure of 15 KPa, and a temperature of a tower top was 35° C. Removed acid, water, and dimer were purified and reused.

A purified oligomer 22 and a depolymerization catalyst stannous octoate 20 were mixed evenly by a depolymerization feed mixer 29, and then the mixture entered a depolymerization reactor 30 for depolymerization reaction under 0.1 KPa at 250° C. The depolymerization reactor 30 was a WEF thin film evaporation reactor, a residence time was controlled to be 1.5 minutes, and a reflux ratio of a depolymerized heavy component 33 was controlled to be 1:1 by a depolymerized heavy component discharging/circulating pump 31. After the refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common tubular heat exchanger of 0.15 m$^2$, and a heat exchange temperature was controlled to be 60° C. After purification, 22.195 g/h lactide product was obtained, with a weight yield of 95.2%, and a content of L-lactide was 96.8%.

Uncondensed steam 39 in a lactide purification reactor 35 entered a recovery system reactor 40, the reactor was a shell-and-tube heat exchanger of 0.15 m$^2$, and a temperature of the heat exchanger was controlled to be 10° C. A recovery liquid was 0.2 g/h lactic acid solution, a concentration of the L-lactic acid was 80%, and the L-lactic acid was reused after purification.

Embodiment 9

90% L-lactic acid raw material 1 entered an oligomerization reactor 6 at a flow rate of 60 g/h through a raw material pump 2. The oligomerization reactor 6 was a RFJL packing reactor, and the reactor was operated at 170° C. under an absolute pressure of 50 KPa for dehydration and oligomerization. A reflux ratio of a dehydrated oligomer was controlled to be 100:1 by an oligomerization discharging/circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 60° C. through reflux. A molecular of an oligomer 9 was 1,500 Da.

The oligomer 9 entered an oligomer purification reactor 18, the reactor was a RFJL packed rectifying tower with side line feeding, and was operated under an absolute pressure of 20 KPa, and a temperature of a tower top was 30° C. Removed acid, water, and dimer were purified and reused.

A purified oligomer 22 and a depolymerization catalyst zinc oxide 20 were mixed evenly by a depolymerization feed mixer 29, and then the mixture entered a depolymerization reactor 30 for depolymerization reaction under 0.1 KPa at 260° C. The depolymerization reactor 30 was a TLNS falling-film reactor, a residence time was controlled to be 1.0 minute, and a reflux ratio of a depolymerized heavy component 33 was controlled to be 0.2:1 by a depolymerized heavy component discharging/circulating pump 31. After the refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common shell-and-tube heat exchanger of 0.25 m$^2$, and a heat exchange temperature was controlled to be 60° C. After purification, 42.851 g/h lactide product was obtained, with a weight yield of 97.2%, and a content of L-lactide was 95.1%.

Uncondensed steam 39 in a lactide purification reactor 35 entered a recovery system reactor 40, the reactor was a plate heat exchanger of 0.25 m$^2$, and a temperature of the heat exchanger was controlled to be 10° C. A recovery liquid was 0.4 g/h lactic acid solution, a concentration of the L-lactic acid was 78%, and the L-lactic acid was reused after purification.

Embodiment 10

85% L-lactic acid raw material 1 entered an oligomerization reactor 6 at a flow rate of 50 g/h through a raw material pump 2. The oligomerization reactor 6 was a RFJL packing reactor, and the reactor was operated at 160° C. under an absolute pressure of 50 KPa for dehydration and oligomerization. A reflux ratio of a dehydrated oligomer was controlled to be 150:1 by an oligomerization discharging/circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 60° C. through reflux. A molecular of an oligomer 9 was 2,500 Da.

The oligomer 9 entered an oligomer purification reactor 18, the reactor was a RFJL packed rectifying tower with side line feeding, and was operated under an absolute pressure of 15 KPa, and a temperature of a tower top was 35° C. Removed acid, water, and dimer were purified and reused.

A purified oligomer 22 and a depolymerization catalyst zinc oxide 20 were mixed evenly by a depolymerization feed mixer 29, and then the mixture entered a depolymerization reactor 30 for depolymerization reaction under 0.2 KPa at 250° C. The depolymerization reactor 30 was a double-falling-film reactor, a residence time was controlled to be 1.0 minute, and a reflux ratio of a depolymerized heavy component 33 was controlled to be 0:1 by a depolymerized heavy component discharging/circulating pump 31. After the refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common plate heat exchanger of 0.2 m$^2$, and a heat exchange temperature was controlled to be 60° C. After purification, 36.644 g/h lactide product was obtained, with a weight yield of 94.3%, and a content of L-lactide was 96.7%.

Uncondensed steam 39 in a lactide purification reactor 35 entered a recovery system reactor 40, the reactor was a spiral plate exchanger of 0.2 m$^2$, and a temperature of the heat exchanger was controlled to be 10° C. A recovery liquid was 0.24 g/h lactic acid solution, a concentration of the L-lactic acid was 75%, and the L-lactic acid was reused after purification.

Embodiment 11

90% L-lactic acid raw material 1 entered an oligomerization reactor 6 at a flow rate of 50 g/h through a raw material pump 2. The oligomerization reactor 6 was a double-falling-film reactor, and the reactor was operated at 160° C. under an absolute pressure of 50 KPa for dehydration and oligomerization. A reflux ratio of a dehydrated oligomer was controlled to be 120:1 by an oligomerization discharging/circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 60° C. through reflux. A molecular of an oligomer 9 was 2,000 Da.

The oligomer 9 entered an oligomer purification reactor 18, the reactor was a RFJL packed rectifying tower with side line feeding, and was operated under an absolute pressure of 15 KPa, and a temperature of a tower top was 35° C. Removed acid, water, and dimer were purified and reused.

A purified oligomer 22 and a depolymerization catalyst zinc oxide 20 were mixed evenly by a depolymerization feed mixer 29, and then the mixture entered a depolymerization reactor 30 for depolymerization reaction under 0.2 KPa at 250° C. The depolymerization reactor 30 was a WEF thin film evaporation reactor, a residence time was controlled to be 1.0 minute, and a reflux ratio of a depolymerized heavy component 33 was controlled to be 0:1 by a depolymerized heavy component discharging/circulating pump 31. After the refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common spiral plate heat exchanger of 0.2 m$^2$, and a heat exchange temperature was controlled to be 60° C. After purification, 36.828 g/h lactide product was obtained, with a weight yield of 94.7%, and a content of L-lactide was 97.3%.

Uncondensed steam 39 in a lactide purification reactor 35 entered a recovery system reactor 40, the reactor was a tubular heat exchanger of 0.2 m$^2$, and a temperature of the heat exchanger was controlled to be 5° C. A recovery liquid was 0.3 g/h lactic acid solution, a concentration of the L-lactic acid was 75%, and the L-lactic acid was reused after purification.

Embodiment 12

90% D-lactic acid raw material 1 entered an oligomerization reactor 6 at a flow rate of 50 g/h through a raw material pump 2. The oligomerization reactor 6 was a double-falling-film reactor, and the reactor was operated at 160° C. under an absolute pressure of 20 KPa for dehydration and oligomerization. A reflux ratio of a dehydrated oligomer was controlled to be 100:1 by an oligomerization discharging/circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 50° C. through reflux. A molecular of an oligomer 9 was 1,400 Da.

The oligomer 9 entered an oligomer purification reactor 18, the reactor was a RFJL packed rectifying tower with side line feeding, and was operated under an absolute pressure of 15 KPa, and a temperature of a tower top was 30° C. Removed acid, water, and dimer were purified and reused.

A purified oligomer 22 and a depolymerization catalyst stannous octoate 20 were mixed evenly by a depolymerization feed mixer 29, and then the mixture entered a depolymerization reactor 30 for depolymerization reaction under 0.2 KPa at 250° C. The depolymerization reactor 30 was a RFJL packing reactor, a residence time was controlled to be 1.5 minutes, and a reflux ratio of a depolymerized heavy component 33 was controlled to be 0:1 by a depolymerized heavy component discharging/circulating pump 31. After the refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common tubular heat exchanger of 0.2 m$^2$, and a heat exchange temperature was controlled to be 60° C. After purification, 36.759 g/h lactide product was obtained, with a weight yield of 94.5%, and a content of L-lactide was 96.1%.

Uncondensed steam 39 in a lactide purification reactor 35 entered a recovery system reactor 40, the reactor was a tubular heat exchanger of 0.2 m$^2$, and a temperature of the heat exchanger was controlled to be 8° C. A recovery liquid was 0.5 g/h lactic acid solution, a concentration of the L-lactic acid was 70%, and the L-lactic acid was reused after purification.

Embodiment 13

90% DL-lactic acid raw material 1 entered an oligomerization reactor 6 at a flow rate of 50 g/h through a raw material pump 2. The oligomerization reactor 6 was a RFJL packing reactor, and the reactor was operated at 170° C. under an absolute pressure of 20 KPa for dehydration and oligomerization. A reflux ratio of a dehydrated oligomer was controlled to be 80:1 by an oligomerization discharging/circulation pump 7, and then the dehydrated oligomer was refluxed to a side line feeding port of the oligomerization reactor 6 for continuous reaction. Lactic acid was refluxed through a rectifying tower 11 at a top of the oligomerization reactor 6, and a temperature of a tower top was controlled to be 50° C. through reflux. A molecular of an oligomer 9 was 1,600 Da.

The oligomer 9 entered an oligomer purification reactor 18, the reactor was a RFJL packed rectifying tower with side line feeding, and was operated under an absolute pressure of 10 KPa, and a temperature of a tower top was 25° C. Removed acid, water, and dimer were purified and reused.

A purified oligomer 22 and a depolymerization catalyst zinc oxide 20 were mixed evenly by a depolymerization feed mixer 29, and then the mixture entered a depolymerization reactor 30 for depolymerization reaction under 0.1 KPa at 250° C. The depolymerization reactor 30 was a WEF thin film evaporation reactor, a residence time was controlled to be 1.5 minutes, and a reflux ratio of a depolymerized heavy component 33 was controlled to be 0:1 by a depolymerized heavy component discharging/circulating pump 31. After the refluxed heavy component was mixed with a new material, the mixture entered the depolymerization reactor 30 again, and a depolymerized light component 34 entered a subsequent purification system.

The depolymerized light component 34 entered a lactide purification reactor 35 after heat tracing transportation, the reactor was a common tubular heat exchanger of 0.2 m², and a heat exchange temperature was controlled to be 60° C. After purification, 36.81 g/h lactide product was obtained, with a weight yield of 94.6%, and a content of L-lactide was 97.7%.

Uncondensed steam 39 in a lactide purification reactor 35 entered a recovery system reactor 40, the reactor was a shell-and-tube heat exchanger of 0.2 m², and a temperature of the heat exchanger was controlled to be 8° C. A recovery liquid was 0.54 g/h lactic acid solution, a concentration of the L-lactic acid was 72%, and the L-lactic acid was reused after purification.

The present invention provides an idea and a method for a synthesis method and device for rapidly producing lactide at high yield, with many methods and ways to realize the technical solution specifically. Those described above are merely the preferred embodiments of the present invention, and it shall be pointed out that those of ordinary skills in the art may further make improvements and decorations without departing from the principle of the present invention, and these improvements and decorations shall also be regarded as the scope of protection of the present invention. All unspecified components in the embodiments can be implemented in the prior art.

What is claimed is:

1. A synthesis device for rapidly producing lactide at high yield, comprising:

an oligomer preparation system (I) used for carrying out a polymerization synthesis reaction with L-lactic acid, D-lactic acid, or DL-lactic acid as a raw material, so as to obtain oligolactic acid, and introducing a reaction product into an oligomer purification system (II);

the oligomer purification system (II) used for purifying the reaction product introduced from the oligomer preparation system (I), removing unreacted lactic acid and water, and introducing the purified oligolactic acid into an oligomer depolymerization system (III);

the oligomer depolymerization system (III) used for depolymerizing the purified oligolactic acid under an action of a catalyst, so as to obtain crude lactide, and introducing the crude lactide into a lactide purification system (IV);

the lactide purification system (IV) used for purifying the crude lactide, so as to obtain a lactide product and a by-product, and introducing the by-product into a recovery system (V); and the recovery system (V) used for processing and utilizing the by-product.

2. The synthesis device for rapidly producing lactide at high yield according to claim 1, wherein the oligomer preparation system (I) comprises an oligomerization reactor (6), a raw material pump (2), an oligomerization catalyst feeding pump (4), a raw material mixer (5), an oligomerization discharging/circulating pump (7), a rectifying tower (11), and a condenser (12);

wherein, a lactic acid raw material (1) and an oligomerization catalyst (3) respectively enter the raw material mixer (5) through the raw material pump (2) and the oligomerization catalyst feeding pump (4) for mixing at the same time, and then the mixture is fed from a side face of the oligomerization reactor (6);

the oligomerization discharging/circulating pump (7) is located on a discharging pipe at a bottom of the oligomerization reactor (6), and is connected with a feeding pipe of the oligomer purification system (II) and a side line feeding port of the oligomerization reactor (6) through a three-way valve;

a feeding pipe of the rectifying tower (11) is connected with a top of the oligomerization reactor (6), a discharging pipe at a top of the rectifying tower (11) is connected with a condensate storage tank (14) after passing through the condenser (12), and a side face of the condensate storage tank (14) is connected with an oligomerization vacuum system (13); and a discharging pipe of the condensate storage tank (14) is provided with a condensate circulating/discharging pump (15), which is connected to a side line feeding pipe of the rectifying tower (11) through a three-way valve.

3. The synthesis device for rapidly producing lactide at high yield according to claim 1, wherein the oligomer purification system (II) comprises an oligomer purification reactor (18), an oligomer discharging pump (19), and a purification condenser (24);

a side line feeding port of the oligomer purification reactor (18) is connected with a discharging pipe of the oligomer preparation system (I); a discharging pipe at a top of the oligomer purification reactor (18) is connected with a purification system condensate storage tank (26) after passing through the purification condenser (24), and a side face of the purification system condensate storage tank (26) is connected with an oligomer purification vacuum system (25); a discharging pipe at a bottom of the purification system condensate storage tank (26) is provided with a purification system condensate discharging pump (27);

the oligomer discharging pump (19) is located on a discharging pipe at a bottom of the oligomer purification reactor (18), and is connected with a feeding pipe of the oligomer depolymerization system (III); and the oligomer purification reactor (18) is a packed rectifying tower.

4. The synthesis device for rapidly producing lactide at high yield according to claim 1, wherein the oligomer depolymerization system (III) comprises a depolymerization reactor (30), a depolymerization catalyst feeding pump (21), a depolymerization feed mixer (29), and a depolymerized heavy component discharging/circulating pump (31);

wherein, a depolymerization catalyst (20) and the purified product produced by the oligomer purification system (II) enter the depolymerization feed mixer (29) through the depolymerization catalyst feeding pump (21) for mixing at the same time, and then the mixture is fed from a side face of the depolymerization reactor (30);

the depolymerized heavy component discharging/circulating pump (31) is located on a discharging pipe at a bottom of the depolymerization reactor (30), and is connected to the depolymerization feed mixer (29) through a three-way valve, a heavy component produced in the depolymerization reactor (30) is returned to the depolymerization feed mixer (29) to be mixed with a reaction raw material, and then the mixture enters the depolymerization reactor (30) again for reaction; and a light component produced in the depolymerization reactor (30) is connected with a feeding pipe of the lactide purification system (IV) through a discharging port above a side face of the depolymerization reactor (30).

5. The synthesis device for rapidly producing lactide at high yield according to claim 1, wherein the lactide purification system (IV) comprises a lactide purification reactor (35) and a lactide storage tank (36);

the lactide storage tank (36) is connected with a discharging port at a bottom of the lactide purification reactor (35), and a lactide product (38) is conveyed outwards through a lactide discharging pump (37); and a by-product discharging port at a top of the lactide purification reactor (35) is connected to a feeding pipe of the recovery system (V).

6. The synthesis device for rapidly producing lactide at high yield according to claim 1, wherein the recovery system (V) comprises a recovery system reactor (40), a recovery liquid storage tank (42), and a recovery liquid discharging pump (43); and a side face of the recovery liquid storage tank (42) is connected with a depolymerization vacuum system (41), and a feeding port at a top of the recovery liquid storage tank is connected with a discharging port at a bottom of the recovery system reactor (40); and the recovery liquid storage tank (42) discharges a recovery liquid (44) outwards through the recovery liquid discharging pump (43) on a discharging pipe at a bottom of the recovery liquid storage tank.

7. The synthesis device for rapidly producing lactide at high yield according to claim 2, wherein the oligomerization reactor (6) or the depolymerization reactor (30) is any one of a falling-film reactor, a thin film evaporation reactor, a packing reactor, and a double falling-film reactor.

8. The synthesis device for rapidly producing lactide at high yield according to claim 5, wherein the lactide purification reactor (35) or the recovery system reactor (40) is any one of a shell-and-tube heat exchanger, a plate heat exchanger, a spiral plate heat exchanger, and a tubular heat exchanger.

9. The synthesis device for rapidly producing lactide at high yield according to claim 4, wherein the oligomerization reactor (6) or the depolymerization reactor (30) is any one of a falling-film reactor, a thin film evaporation reactor, a packing reactor, and a double falling-film reactor.

10. The synthesis device for rapidly producing lactide at high yield according to claim 6, wherein the lactide purification reactor (35) or the recovery system reactor (40) is any one of a shell-and-tube heat exchanger, a plate heat exchanger, a spiral plate heat exchanger, and a tubular heat exchanger.

11. A method for producing a lactide with the synthesis device of claim 1 comprising the following steps
(i) in the oligomer preparation system (I), using L-lactic acid, D-lactic acid, or DL-lactic acid as a raw material, carrying out a polymerization synthesis reaction at 100° C. to 180° C. under an absolute pressure of 1 KPa to 100 KPa, improving a yield by recovering lactic acid from a light component, and improving a molecular weight of oligolactic acid through reflux a heavy component, so as to obtain oligolactic acid with a weight-average molecular weight of 500 Da to 3,000 Da;
(ii) in the oligomer purification system (II), purifying the oligolactic acid obtained in step (1) to remove unreacted lactic acid and water;
(iii) in the oligomer depolymerization system (III), depolymerizing the oligolactic acid purified in step (2) under an action of a catalyst at 200° C. to 260° C. under an absolute pressure of 0.1 KPa to 1 KPa, purifying and collecting the light component to obtain the crude lactide, and refluxing and depolymerizing the heavy component again;
(iv) in the lactide purification system (IV), performing heat exchange for the crude lactide with a tubular heat exchanger of 0.1-0.25 m$^2$ at the temperature between 20° C. and 60° C. to obtain the lactide product and the by-product; and
(v) in the recovery system (V), performing heat exchange for the by-product with a shell-and-tube heat exchanger of 0.1-0.25 m$^2$ at the temperature between −20° C. and 40° C. to obtain a recovery liquid.

12. The method according to claim 11, wherein in step (i), the polymerization synthesis reaction is carried out in the presence of an oligomerization catalyst, and the oligomerization catalyst is any one of zinc oxide, zinc lactate, zinc acetate, zinc isooctanoate, zinc stearate, stannous oxide, stannous oxide, stannous octoate, or stannous chloride.

* * * * *